United States Patent [19]

Belchamber et al.

[11] Patent Number: 5,040,734

[45] Date of Patent: Aug. 20, 1991

[54] METHOD FOR DETERMINING PHYSICAL PROPERTIES

[75] Inventors: Ronald M. Belchamber, Berkshire; Patrick Collins, Middlesex, both of England

[73] Assignee: The British Petroleum Company p.l.c., London, England

[21] Appl. No.: 492,261

[22] Filed: Feb. 28, 1990

Related U.S. Application Data

[63] Continuation of Ser. No. 246,239, Sep. 16, 1988, abandoned.

[51] Int. Cl.⁵ .................. B02C 23/00; B02C 25/00
[52] U.S. Cl. ................................ 241/30; 241/33
[58] Field of Search .................. 241/30, 33, 34, 36; 267/908

[56] References Cited

U.S. PATENT DOCUMENTS

| | | | |
|---|---|---|---|
| 2,136,907 | 11/1938 | Roder | 241/34 |
| 2,824,701 | 2/1958 | Vester et al. | 241/34 X |
| 2,833,482 | 5/1958 | Weston et al. | 241/30 |
| 3,314,614 | 4/1967 | Daniel et al. | 241/34 X |
| 4,026,479 | 5/1977 | Bradburn et al. | 241/33 X |
| 4,210,290 | 7/1980 | Andersson et al. | 241/30 |
| 4,480,480 | 11/1984 | Scott et al. | |
| 4,559,828 | 12/1983 | Liszka | |
| 4,597,535 | 7/1986 | Fontanille | 241/34 X |
| 4,611,763 | 9/1986 | Tomiyasu et al. | 241/30 |
| 4,691,869 | 9/1987 | Onuma et al. | 241/34 |

FOREIGN PATENT DOCUMENTS

1564201  4/1980  United Kingdom .

Primary Examiner—Joseph M. Gorski
Attorney, Agent, or Firm—Larry W. Evans; Joseph G. Curatolo; Teresan W. Gilbert

[57] ABSTRACT

A method for the determination of the value of a property of the material within a mill during the comminution of solid material within the mill comprises the steps of:

(a) detecting the noise intensity of milling by means of an analog electrical signal, the intensity of which is proportional to the intensity of the noise in the audio frequency range, (b) converting the analog signal to a digital signal, (c) passing the digital signal through a digital bandpass filter to select at least two frequency bands, and (d) analyzing the data from the bands by means of a multivariate statistical technique to obtain the value of the property. The method is particularly suitable for determining the particle size distribution of material being ground in a ball mill.

11 Claims, 16 Drawing Sheets

METHOD FOR DETERMINING PHYSICAL PROPERTIES

This is a continuation of co-pending application Ser. No. 07/246,239 filed on Sept. 16, 1988, now abandoned.

This invention relates to a method for non-intrusively determining the physical properties of material in a mill during size reduction operations (comminution).

Comminution of solid materials, particularly minerals, is a frequently performed operation. For instance, some mineral ores are crushed and ground prior to extraction of the metal, pigments before addition to paints, and coal is similarly treated prior to combustion in large scale industrial furnaces. Equipment used during comminution is generally classified in three categories, coarse mills such as jaw crushers, intermediate mills such as disc crushers and hammer mills, and fine mills such as roller mills, ball mills and rod mills.

Crushing and grinding are energy intensive processes. It has been estimated that they consume about 5% of the world's energy output. In minerals processing, comminution is by far the largest operating cost. For example, in a survey of a number of Canadian copper concentrators, it was found that the average power consumption in KWh/tonne was 2.2 for crushing, 11.6 for grinding and 2.6 for flotation.

Commercial mills are usually indirectly controlled by sampling the ground material and measuring the slurry density or the viscosity off-line. This approach is unsatisfactory because the plant is controlled by out of date information.

For batch milling a direct, real-time measure of the particle size distribution is desirable for optimum grinding.

It would be advantageous to provide this information on-line and in real time.

Sound is generated during comminution. This is usually considered to be an undesirable attribute of these processes.

We have now discovered that the frequency distribution of mill sound (acoustic frequency distribution) can be related to the properties of the material being milled and thus an apparent disadvantage can be turned to a positive benefit.

Thus, according to the present invention there is provided a non-intrusive method for the determination of the value of a physical property of the material within a mill during the comminution of solid material within the mill which method comprises the steps of:

(a) detecting the acoustic frequency distribution of milling by means of a sound transducer, e.g. a microphone, the output from which is an analogue electrical signal, the intensity of which is proportional to the intensity of the sound in the audio frequency range, (b) converting the analogue signal to a digital signal, (c) passing the digital signal through a digital bandpass filter to select at least two frequency bands, (d) averaging the power in the bands for a specified period of time, and (e) analysing the acoustic power in the bands by means of a multivariate statistical technique to obtain the value of the property.

If necessary, the analogue electrical signal can be amplified and/or passed through a band-pass filter to remove frequencies above, say, 10 KHz to prevent aliasing, and below, say, 50 Hz to remove spurious low frequency signals.

The digital band pass filter is preferably capable of selecting from two to twenty four desired frequency bands.

The properties which may be determined include those variables which fully characterise the material in a mill, namely, the particle size distribution of the solid particles and, when wet milling is employed, the pulp density (solid:liquid ratio) and the pulp volume (volume of solid and liquid). Other parameters of interest may be calculated from these.

Suitable multivariate statistical techniques are the methods of principal components analysis (PC) and partial least squares (PLS).

PC analysis is a numerical technique which allows multivariate data to be displayed in two dimensions for ease of interpretation. The PC's are vectors which are linear combinations of the original features and take the form:

$$Y_j = A_{1j}X_1 + A_{2j}X_2 + \ldots + A_{nj}X_n$$

where
$Y_j$ = jth principal component
$X_n$ = feature
$A_{nj}$ = coefficient

The PC's are all orthogonal and equal in number to the measured features. The coefficients of the vectors are calculated so that most of the variance in the data is expressed in the first few PC's whilst the relative magnitude of the coefficient reflects the discriminatory power of the original features. By transforming the data using equations of the above type the data may be plotted in a low dimensional form.

PLS analysis allows the relationship between sets of data (which are related or where it is expected that a relationship exists) to be empiricially modelled. Two 'training sets' of data (in this case particle size distribution and AE (Acoustic Emission) frequency distribution) are used to generate the model. Having developed the model, validation is carried out. 'Test sets' of data, acquired under the same conditions but not used to build the model, are then input. Where actual values are known, the errors between these and the values generated are used to validate the accuracy of the model's predictions. If one set is unknown PLS is able to predict values from knowledge of the other, using the model.

For more details of the statistical methods which may be used, see for example the textbooks; "MULTIVARIATE ANALYSIS," Wold. H., Academic Press, New York, 1966, Krishnaiah, P. R. (Ed.) and Sharaf, M. A., Illman, D. L. and Kowalski, B. R., "CHEMOMETRICS", John Wiley and Sons Inc., New York, 1986, (Elving, P. J., Winefordener, J. D., and Kolthoff, I. M., eds)

The method is applicable to any type of milling machine including batch machines and continuous machines where mill efficiency is influenced by the amount and particle size distribution of the feed material. It is particularly suitable for use with ball mills.

It provides means for determining on-line and non-invasively particle size distributions, pulp densities and pulp volumes in near "real time".

The invention is illustrated with reference to FIGS. 1 to 16 of the accompanying drawings and the following Examples.

2—the change in particle size distribution during experiment 6.

3—the change in spectra during experiment 6.

4—the normalised start and finish spectra from experiment 6.

5—changes made in pulp volume and pulp density during experiment 1.

6—changes in spectra during first 50 minutes of experiment 1.

7—changes in spectra during experiment 1.

8—changes made in pulp volume and pulp density during experiment 4.

9—changes in spectra during experiment 4.

10—PC plot of acoustic data from experiments 1-5.

11—PLS plot of predicted and measured pulp volume and % sand for 10 randomly selected test samples.

12—PLS plot of predicted and measured particle size values (% under by mass) for 10 randomly selected test samples.

13—PLS predicted and measured particle size values (% under w/w) for 10 randomly selected test samples.

14—particle size change during continuous milling.

15—specific gravity change during continuous milling.

16—selected acoustic spectra changes during continuous milling.

Figure 1:
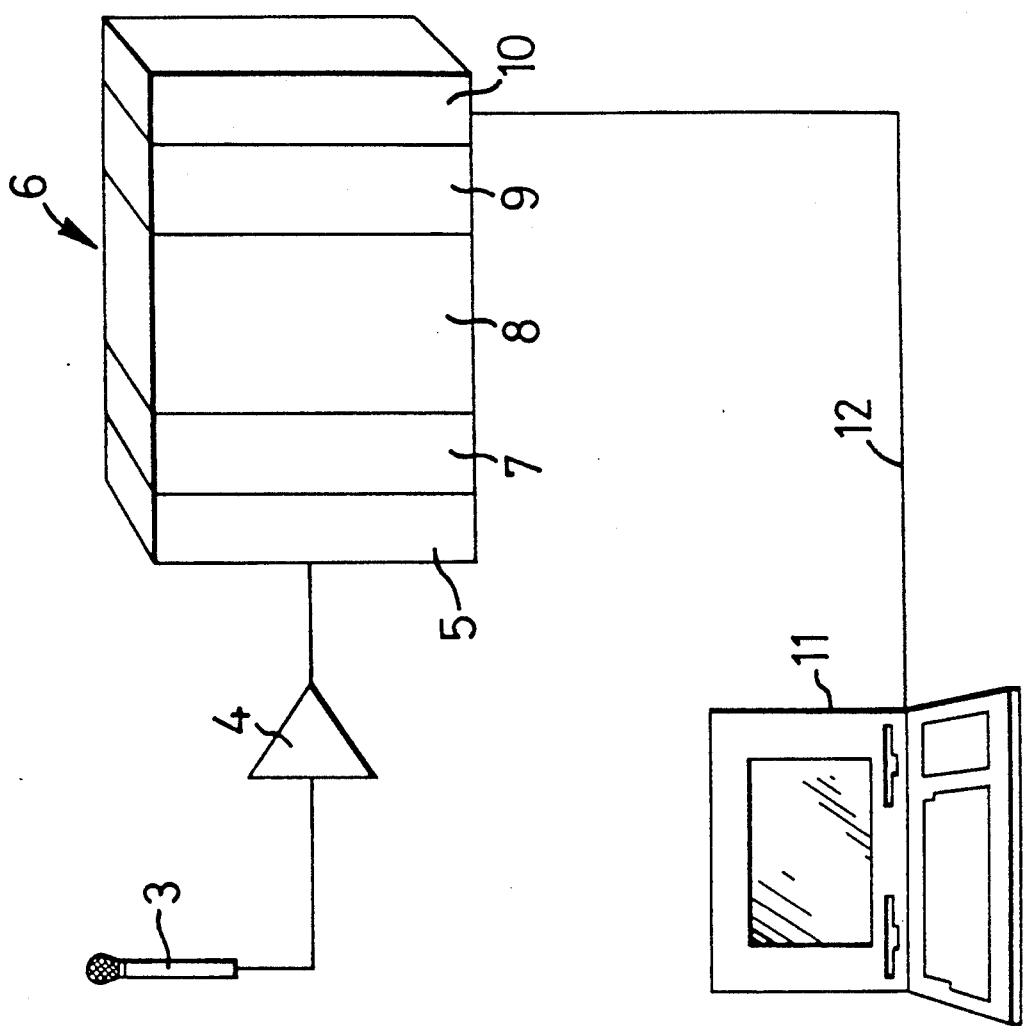
FIG. 1 is a schematic diagram of apparatus for use in the method according to the present invention.

With reference to FIG. 1, sharp sand was ground in a batch British Rema 0.61 m diameter×0.92 m length ball mill 1 driven by an electric motor 2. The grinding medium was 16 mm diameter steel balls, filling (including voids) about 40% of the mill volume.

The sound intensity of grinding was picked up by a flat frequency response audio-microphone 3. This has a Bruel and Kjaer, Type 4165 cartridge and a Type UA0308 dehumidifier and was mounted in a fixed position close to the mill. It had a flat ($\pm 1$ dB) frequency response up to 10 KHz.

Electrical signals from the microphone were amplified using a Rhomicron Instruments MAPS 1 preamplifier 4.

The amplified signals were then analysed by a third octave analyser 6 (Data Beta, DBDTO-10). This comprises an analogue-to-digital converter 7 front-ended with a 12.5 KHz low pass anti-aliasing filter 5, a digital band-pass filter 8, a central processing unit (CPU) 9 and an RS-232 serial line interface 10. The band-pass filter uses a series of digital filters to divide the region 50 Hz to 10 KHz into 24 bands. The averages the power in each of these bands for a specified period. In all cases 10 seconds averaging times were used.

The system is controlled by an IBM PC-AT computer 11 linked to the serial line 10 by means of a cable 12.

Frequency data was analysed using a multivariate statistical technique implemented on the microcomputer 11.

Batch Milling Experiments 1-6

The batch mill described with reference to FIG. 1 was used. The charge used in these experiments was sharp sand. In order to investigate the widest range of milling conditions experiments were carried out in which the pulp density and volume were altered according to an experimental design. Table 2 shows the initial, intermediate and final conditions for each of the experiments.

For example, in experiment 1, the mill was filled to the 120% level (100% full is defined as completely filling the voids between the balls) with a sharp-sand/water mixture (sand 40% by volume). As the milling progressed the mill was stopped at 5 minute intervals and a measured volume of pulp was removed from the mill. This effectively reduced the volume while not affecting the density. On reaching a pulp volume of 90%, aliquots of water were added to the mill, with the effect of increasing the pulp volume and reducing the pulp density (eventually to 119% and 25% respectively). The experiment was concluded with the addition of unground sharp sand to the mill, to introduce a bimodal distribution in the particle size, and the contents were milled for a further 35 minutes (final pulp volume and density were 92% and 40% respectively). In the 6th experiment only very small samples of pulp were removed so that the pulp density and volume were held effectively constant. This experiment was designed to study the effects of particle size only. Milling conditions in experiment 6 (in terms of ball charge and mill rotation speed) were different to the conditions in experiments 1 to 5. For this reason the results of experiment 6 were not used as part of the 'PLS model training set' described later.

The samples of slurry removed from the mill were used to estimate the particle size distribution and pulp density. Particle size measurements were made using a combination of sieving, for particle diameters ranging from 125 to 1000 microns, and a Malvern (laser diffraction) sizer for sub-125 micron particles. Percentage undersize by weight was determined for 12 particle diameters (1000, 500, 250, 125, 87.2, 53.5, 28.1, 16.7, 10.1, 6.2, 3.8 and 1.9 microns).

ANALYSIS OF ACOUSTIC SIGNALS

The relationships between the acoustic emission frequency distribution to the particle size distribution, pulp density and volume were explored using two multi-variate statistical techniques; principal components analysis and partial least squares modelling (PC and PLS).

EFFECT OF PARTICLE SIZE DISTRIBUTION

Figure 2:
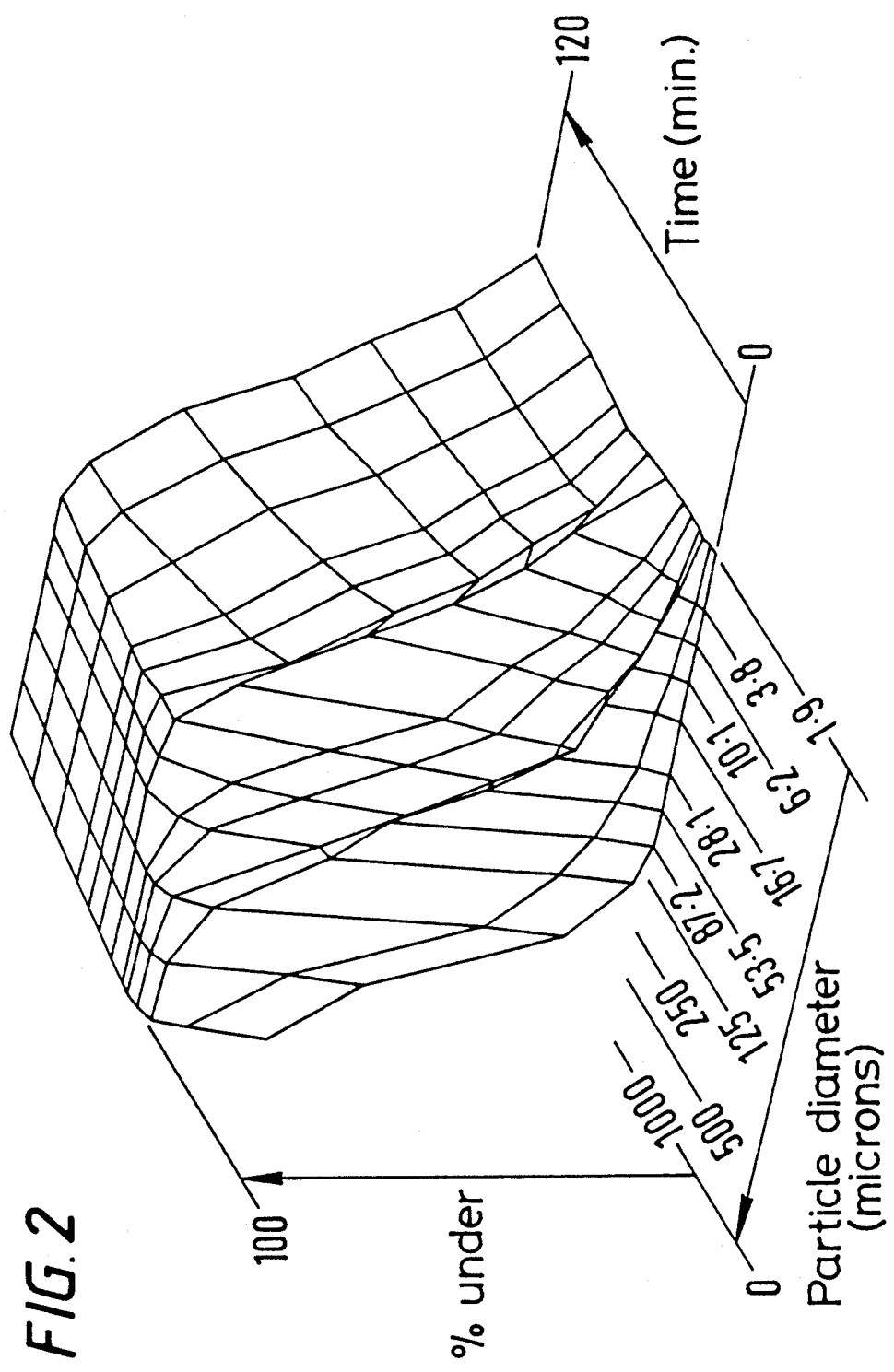
FIGS. 2 to 16 are diagrams showing respectively
Figure 3:
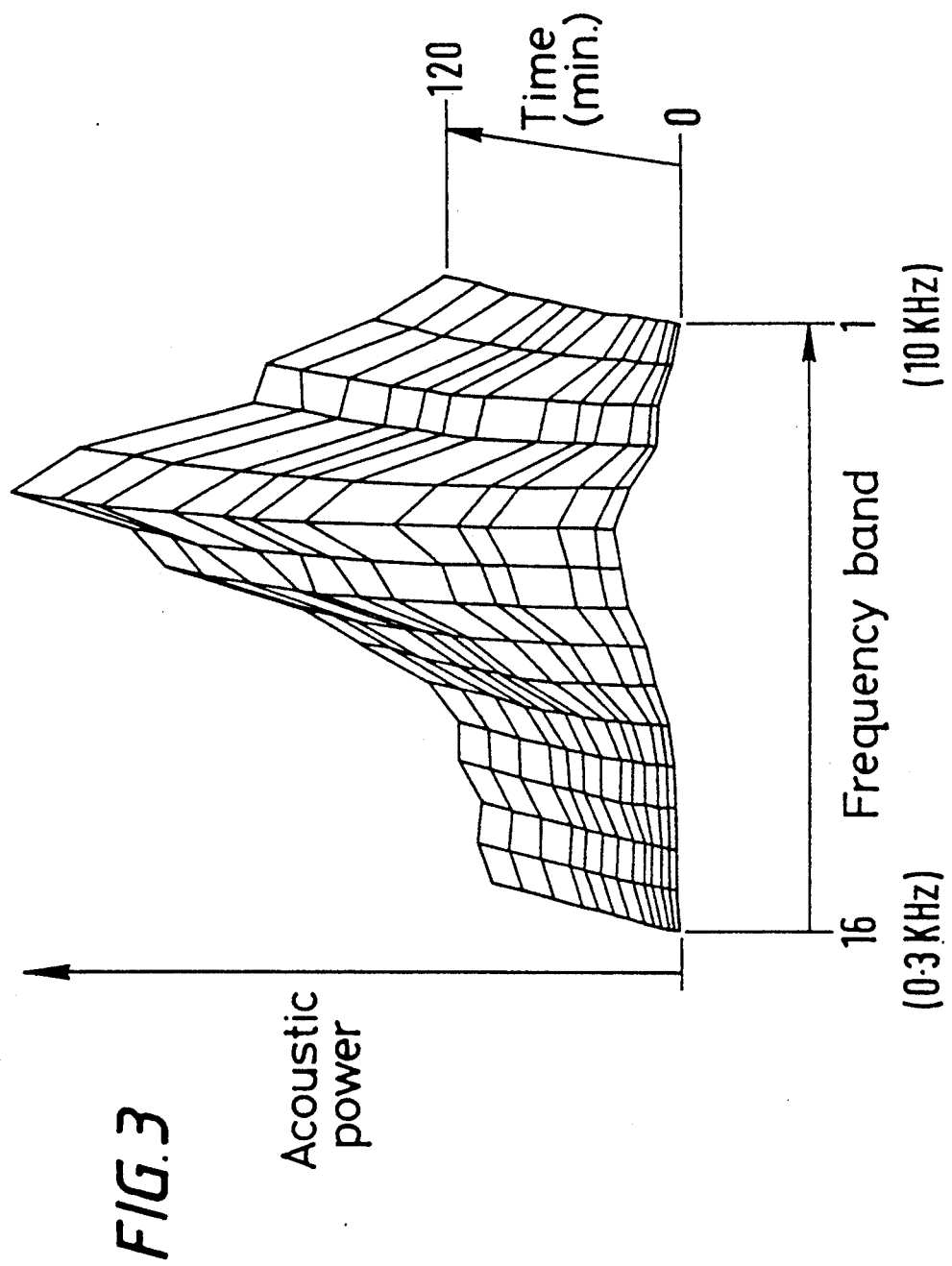

The particle size distribution in the mill mainly influences the overall amplitude of the acoustic emission. As the particle size is reduced the acoustic emission increases in amplitude. This increase is more pronounced in the higher frequency bands. This is illustrated by the results from experiment 6 in which the pulp volume and density were held constant (FIG. 2) and the particle size decreased with time. As comminution progressed acoustic power increased across the whole of the frequency range (FIG. 3).

Figure 4:
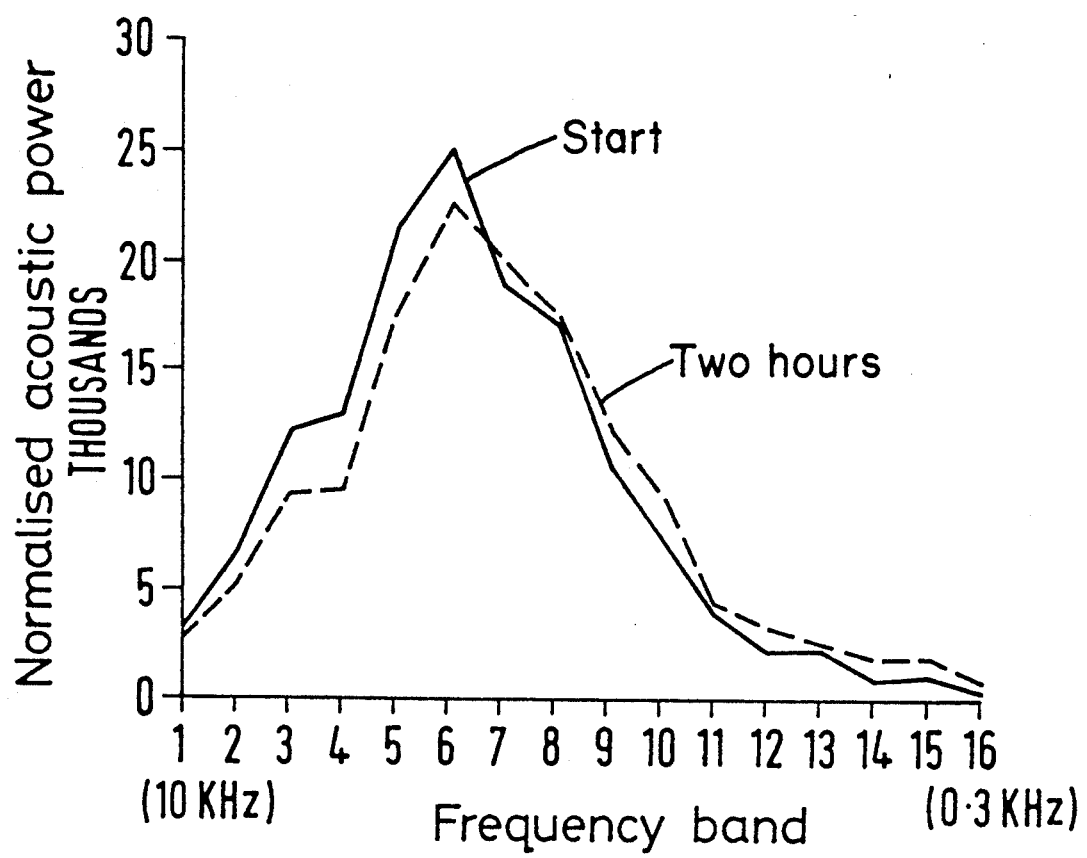

The peak acoustic power remains in band 6 (3.1 KHz) throughout the experiment, however the distribution becomes skewed towards higher frequencies (FIG. 4).

Audio noise produced by a ball mill appears to be largely due to collisions between the balls and between balls and the mill liner. The presence of mineral particles reduce the impact velocity of the balls, the larger particles having the greater effect.

EFFECT OF PULP VOLUME

Changing the volume of material in the mill has two effects on the acoustic frequency distribution. Firstly, as the volume is increased the overall emission intensity decreases. Secondly, the acoustic power shifts to lower frequencies.

Figure 5:
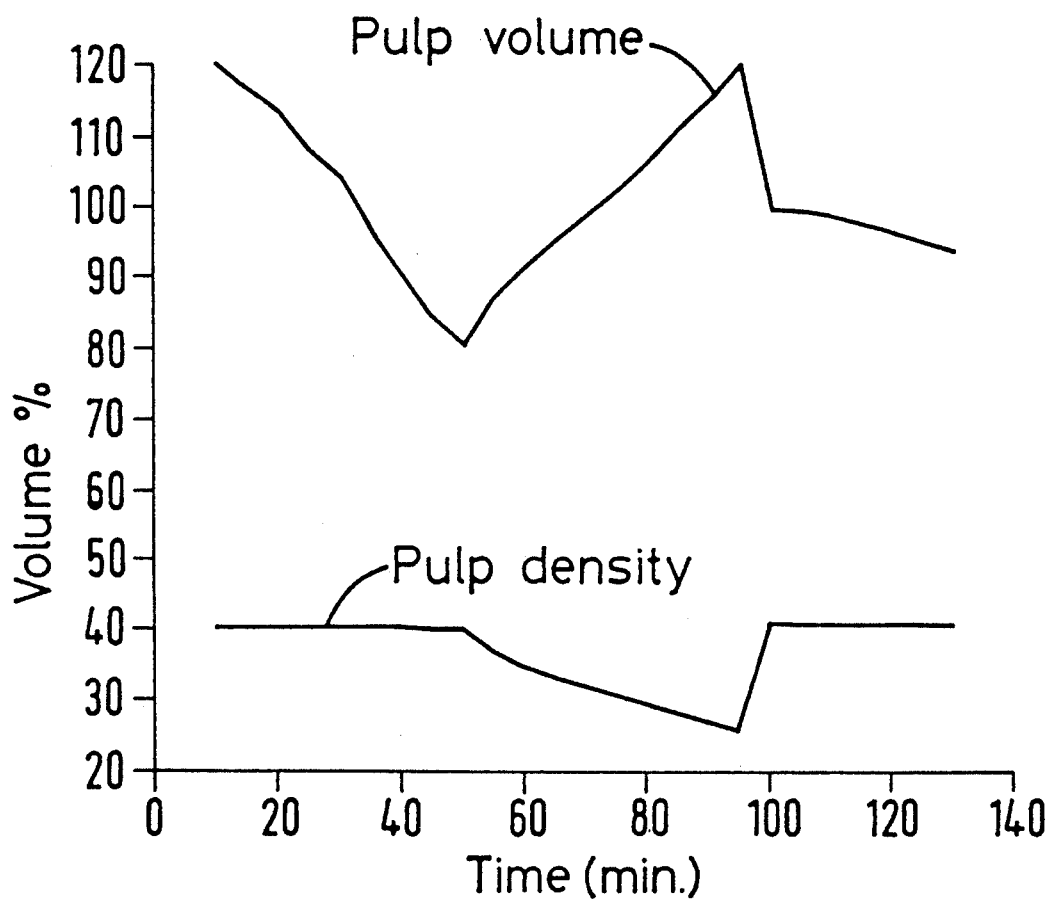

The results obtained from experiment 1 illustrate these trends. In the first stage of the experiment (0-50 min) the pulp volume was changed from 120% to 80% (FIG. 5).

Figure 6:
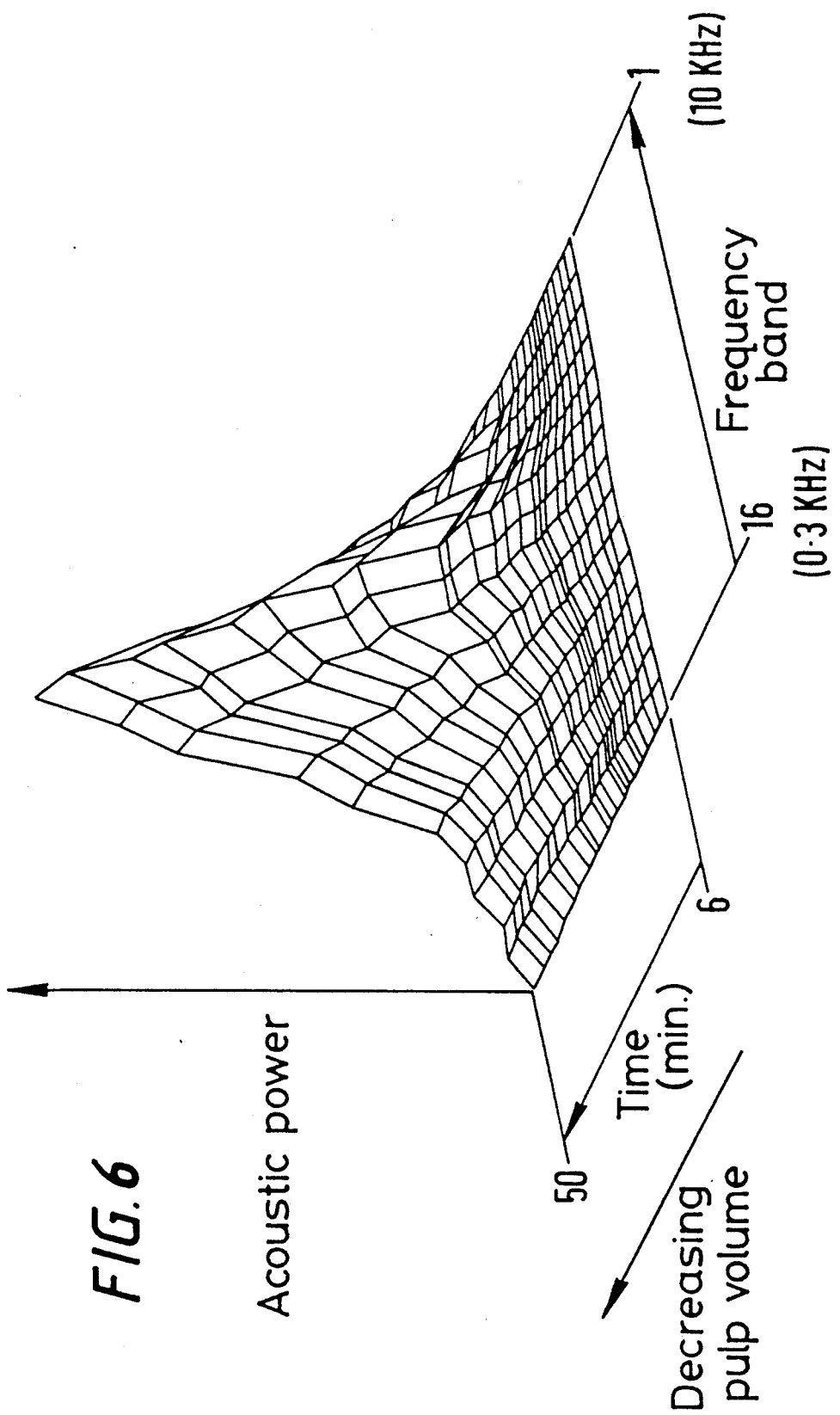
Figure 7:
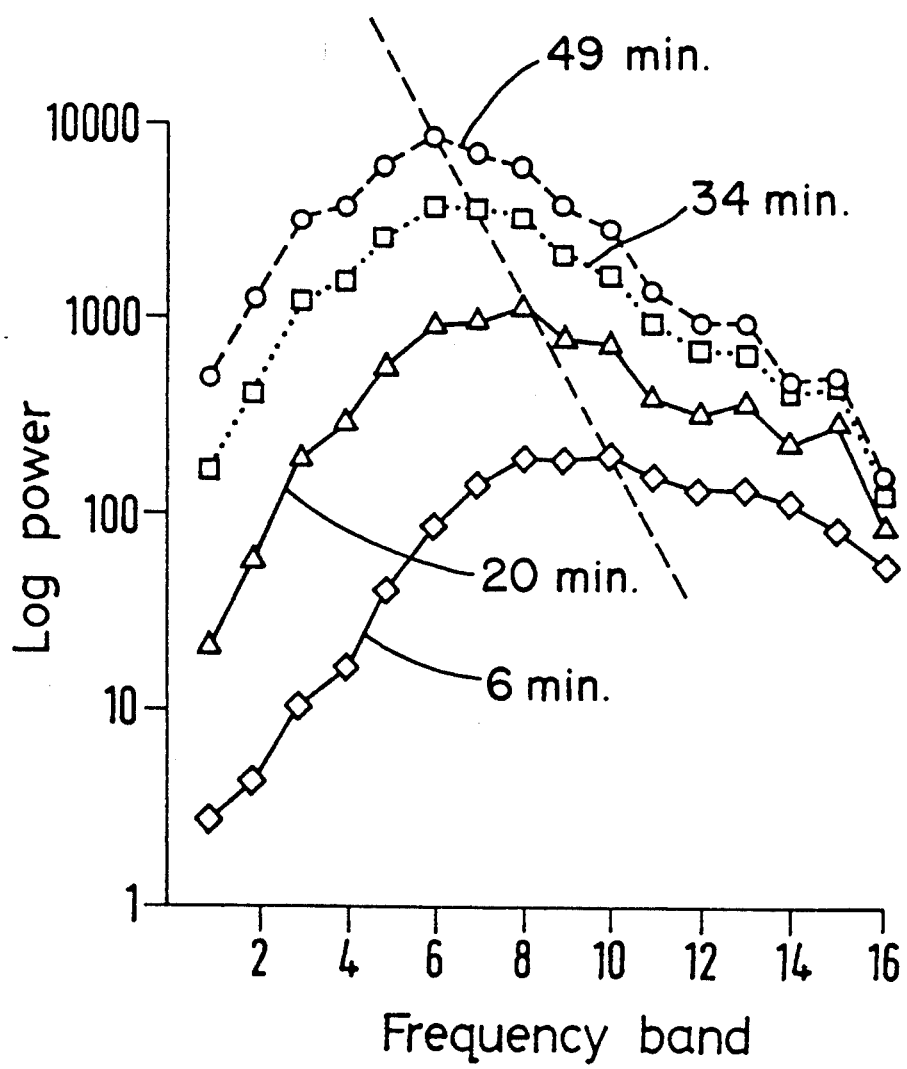

As the pulp volume was reduced the amplitude of the acoustic spectrum increased rapidly (FIG. 6). This is due to a combination of comminution of the sand (particularly fast, in terms of particle diameter, in the early stages of milling) and the reduced damping effect as pulp is removed from the mill. At 120% capacity, the peak power is in band 10 (1.25 KHz). As the pulp volume is decreased the peak power shifts to higher frequencies. At 100% full, peak power was in band 6 (3.15 KHz). Reducing the pulp volume below 100% increases only the amplitude of the emissions and has no further effect on the peak power frequency (FIG. 7).

EFFECT OF PULP DENSITY

Increases in the pulp density cause the amplitude of the acoustic spectrum to decrease but have a less pronounced effect on the frequency distribution. The relationship is complex. This is further complicated by the fact that pulp density changes are accompanied by changes in volume and progressive comminution.

Figure 8:
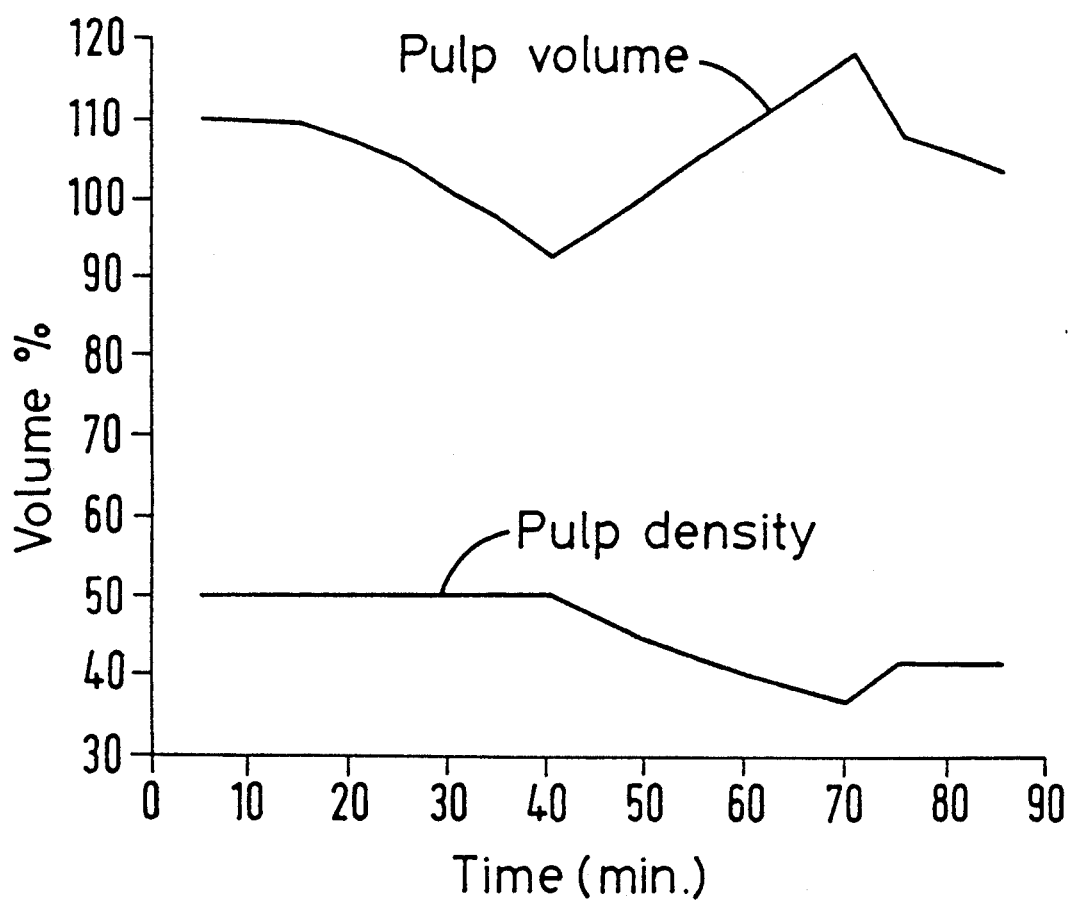
Figure 9:
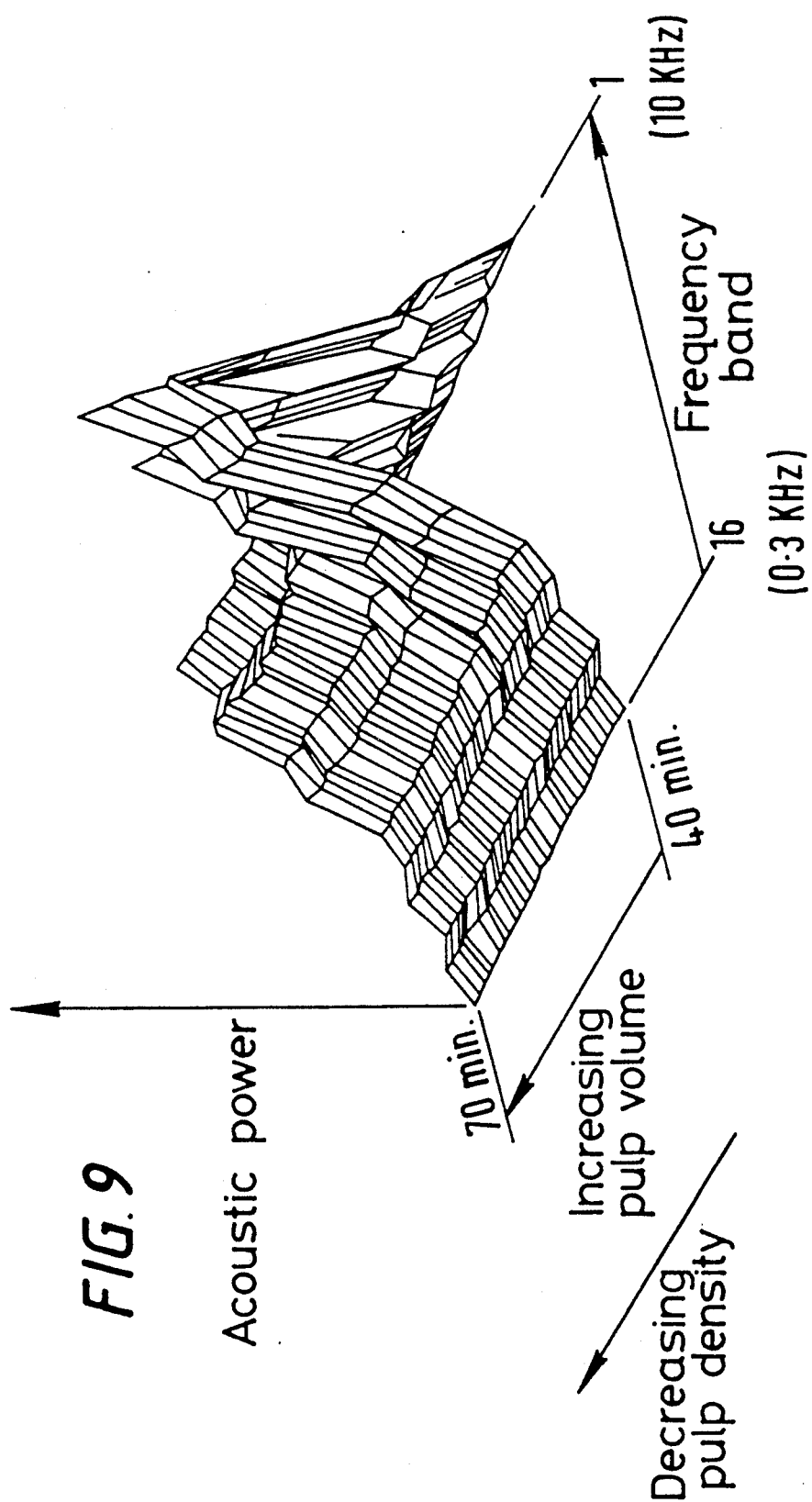

These effects are shown in FIGS. 8 and 9. Between 40 and 70 minutes the pulp density was reduced from 50% to 36% by adding, at five minute intervals, aliquots of water, thereby increasing the pulp volume from 92% to 118%. The reduction in acoustic emission power which normally accompanies decreasing volume in the mill (compare FIGS. 9 and 6) is, in this case, opposed by the effects of a decreasing pulp density. Therefore one may conclude that lowering the pulp density increases the acoustic emission amplitude.

QUANTITATIVE CORRELATION OF ACOUSTIC SIGNAL MILL VARIABLES

Figure 10:
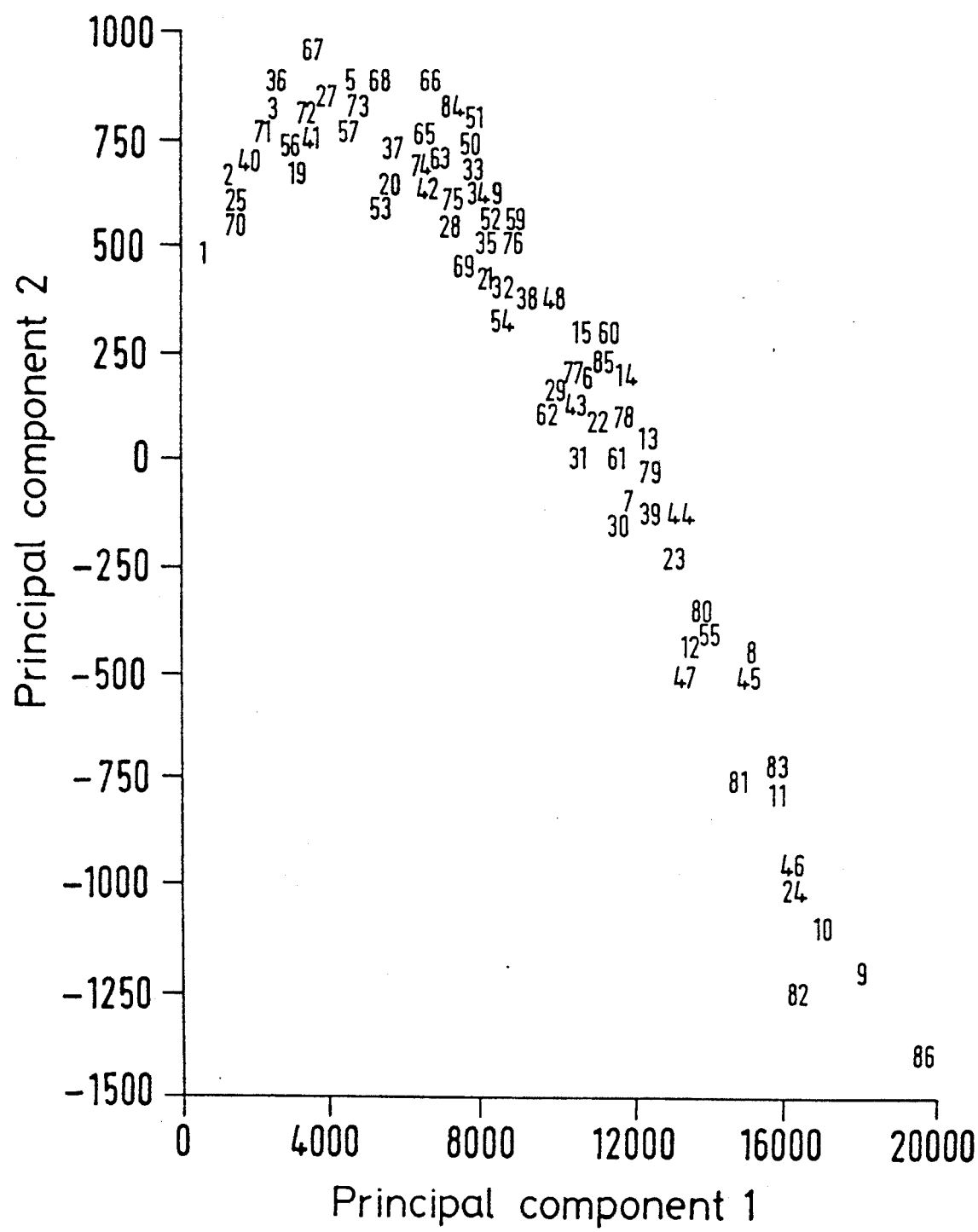

Principal components analysis was used to investigate the multivariate acoustic emission data. Sixteen acoustic features were selected, where features 1 to 15 corresponded to the power in each of the 3rd octave bands shown in Table 1. The 16th feature was a combination of the remaining 8 (312 to 49 Hz) third octaves. FIG. 10 shows how the acoustic data collected from batch experiments 1 to 5 was distributed. The numbers represent individual power spectra obtained at different times during the batch experiment. Principal component (PC) 1, which accounts for most of the variance in the data, is a measure of the amplitude of the acoustic emission. PC 2 is a measure of the mean frequency of the signal. The change in direction at the top of the plot corresponds to a reverse in frequency shift direction and is associated with lower acoustic power conditions. This suggests that for quantitative analysis, ideally, two models should be used to cover the full range of mill operating conditions.

PLS MODELLING AND VALIDATION OF RESULTS

The data obtained from these experiments were analysed by PLS. A model was developed to relate the 16 variables in the acoustic data set to the 14 variables in the milling data set (12 particle diameters, pulp volume and pulp density). A total of 76 samples was used to build the PLS model which included the bimodal distribution data acquired in the latter stages of each experiment. A further 10 samples (randomly sampled from batch experiments 1 to 5), none of which had been used in the model building stage, were selected to validate the performance of the model.

Figure 11:
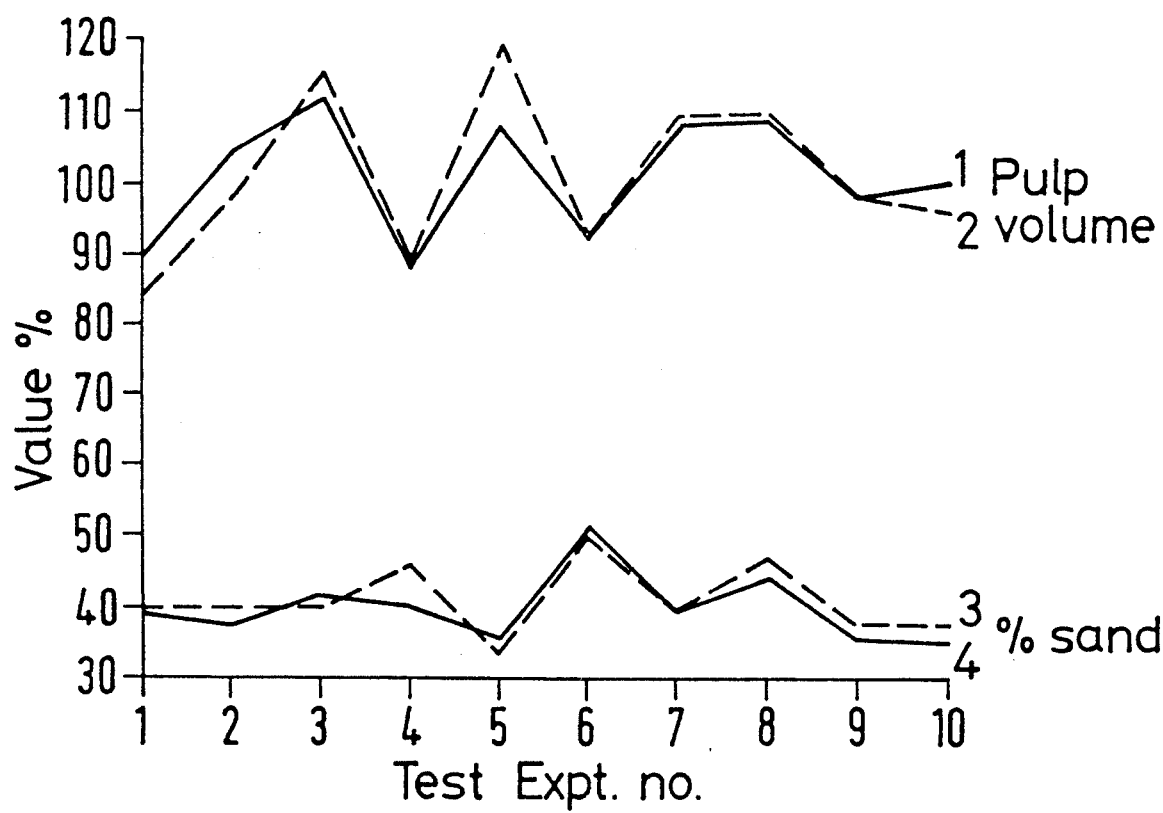
Figure 12:
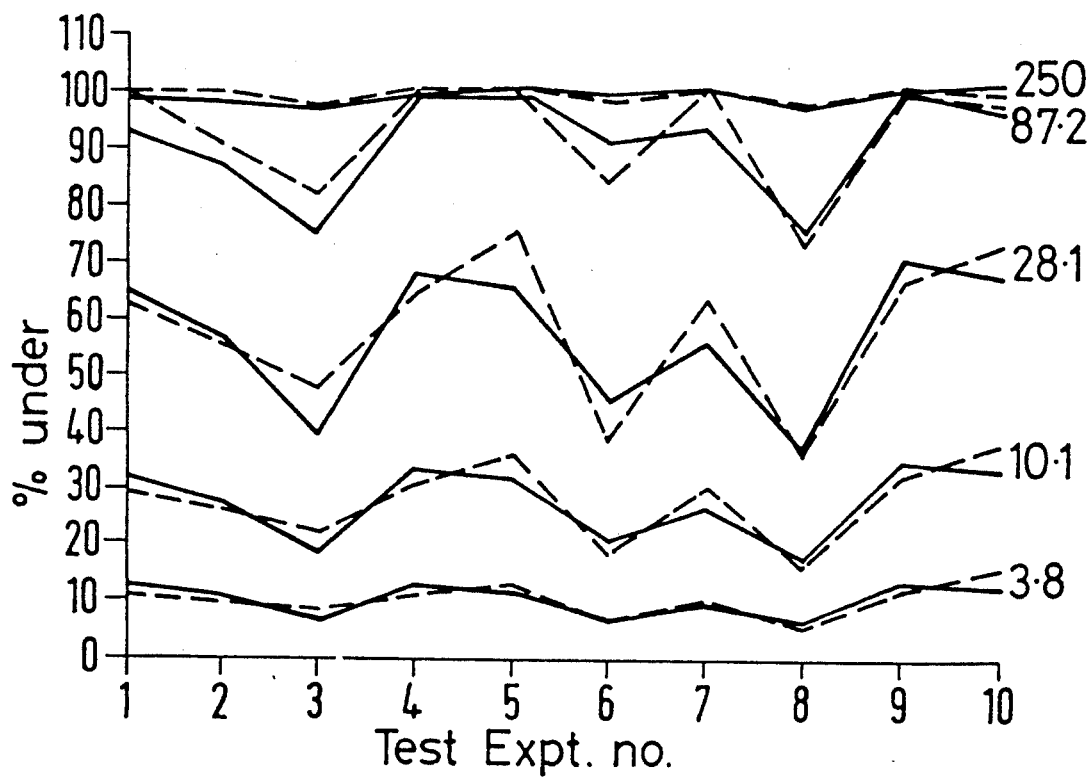
Figure 13:
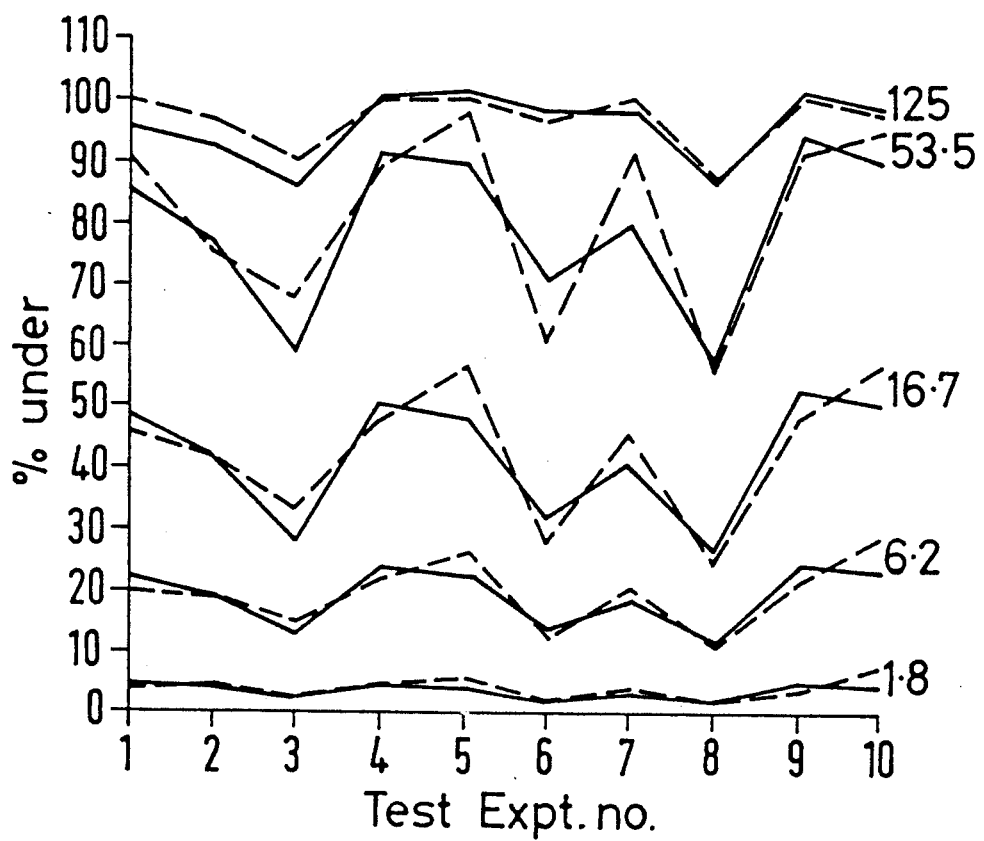

A comparison of the PLS predictions of the pulp volume, pulp density and the measured particle size distribution are shown graphically in FIGS. 11-13. FIGS. 11 and 12 shown ten particle size distributions for particle diameters ranging from 250 to 1.9 microns. (The joining of the points on these graphs has no mathematical significance and is merely a visual aid). The PLS predictions for the particle size distributions compare well with those obtained by sieving and laser diffraction. FIG. 13 shows the PLS prediction of pulp volume and pulp density compared with those values which have been calculated and measured respectively.

CONTINUOUS MILLING EXPERIMENT 7

The batch ball mill of experiments 1-6 was replaced by a continuous feed 0.6 m diameter × 1.0 m length mill. The grinding medium was a mixture of steel balls ranging in size from 25 to 70 mm. A quartz ore was selected for study.

The experimental strategy was similar to that of the batch experiments in that a wide range of milling conditions was investigated, this time by controlling solid feed and water flow rates. Samples of slurry were taken at regular intervals for pulp density and particle size measurement. Acoustic data was sampled continuously during the operation of the mill.

Acoustic data was collected continuously from the ball mill for a period of 15.2 hours. At intervals (typically 20 minutes), samples of the output stream were taken for analysis (total 34). For practical reasons only one particle size diameter (% under 180 microns) and specific gravity were measured for each sample. Changes in milling conditions were effected by altering the feed rate of the mineral and the water flow rate. In these experiments it was assumed that the mill operation acted as a perfect mixer. In an industrial scale operation it would be necessary to calculate the mill composition from knowledge of the flow rates and particle size distributions of the mill feed and the product, using a suitable grinding simulation package.

Figure 14:
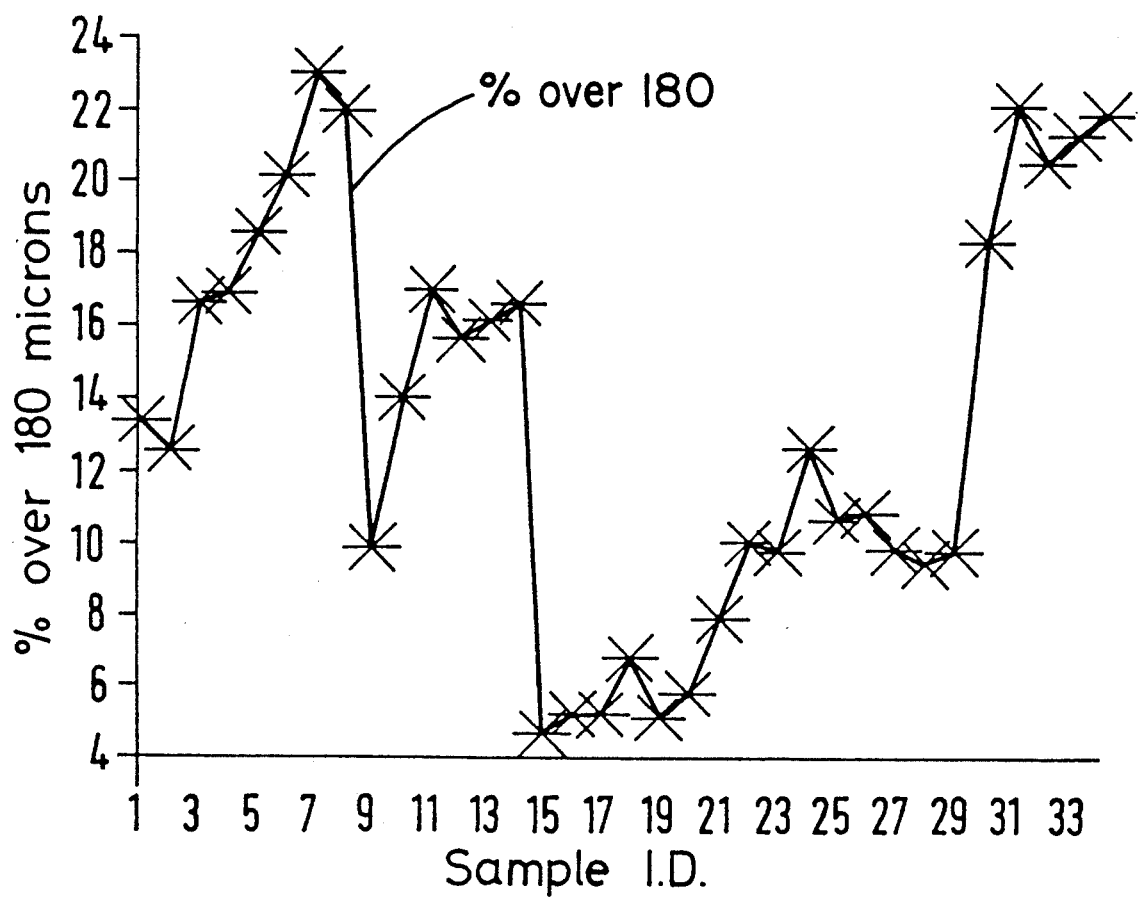
Figure 15:
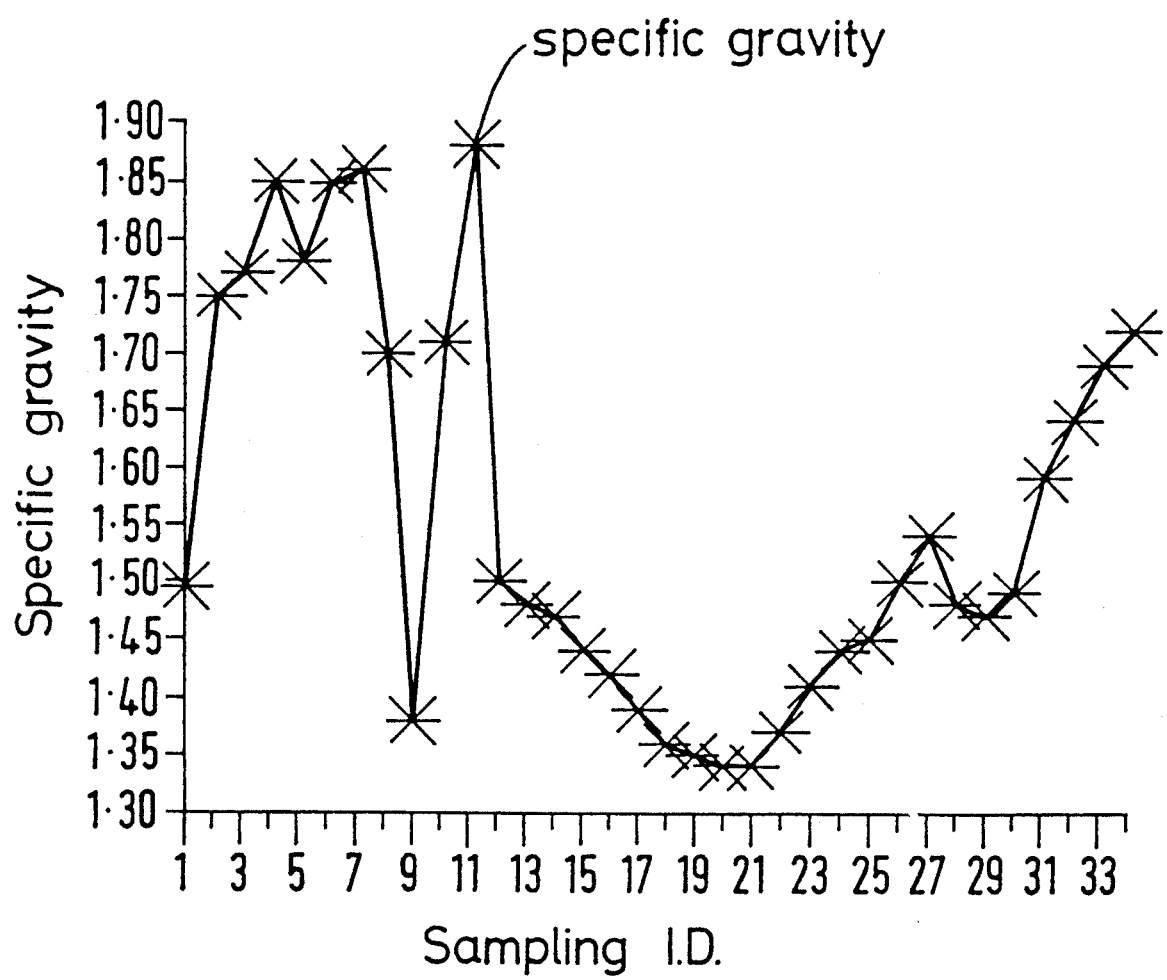
Figure 16:
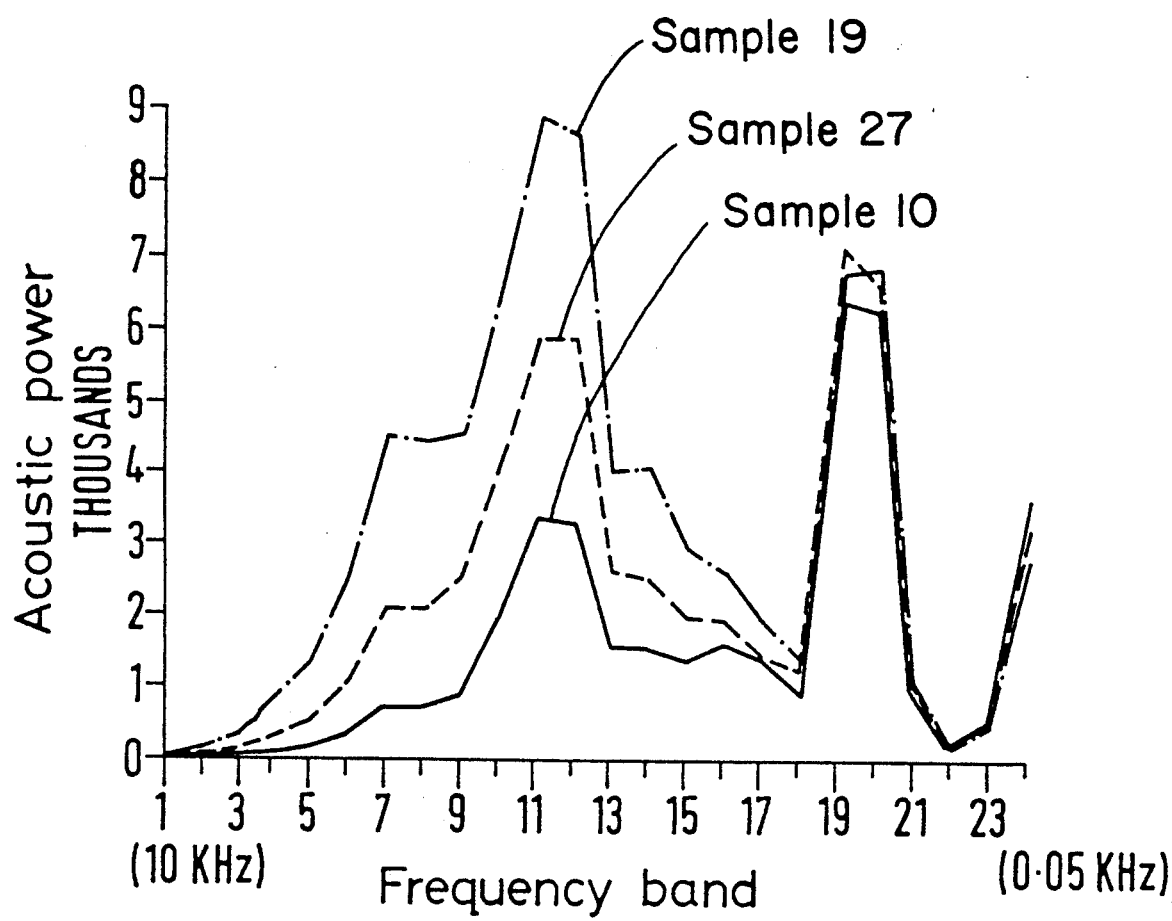

FIGS. 14 and 15 illustrate how particle size and specific gravity changed during milling. In these experiments the mill was operated over a wide range of conditions to see whether the acoustic spectra were influenced by milling parameters in a similar manner to batch acoustic spectra. As expected, this was indeed the case. For example acoustic spectra show similar trands in amplitude and frequency to those observed in the batch experiments. The dominant bands have shifted to lower frequencies (band 11, 1 KHz). The second peak (bands 19, 20) at 150 Hz was not influenced significantly by the milling conditions and was subsequently found to originate in the gearbox driving the mill.

Principal components analysis of the acoustic data reveals systematic trends which are very similar to those found in the batch experiments. This indicates that the technique is suitable for monitoring continuous processes.

The results from these experiments show:

(a) The audio acoustic emission character of a batch or continuous mill is dependent on the particle size distribution, the pulp density and volume.

(b) The exact physical relationship between the acoustic emission and the milling parameters is complex. An empirical modelling approach (PLS) enables the milling parameters to be estimated from the acoustic emissions without the need for a physical model.

(c) The PLS algorithm is very rapid, being able to compute on a micro-computer the particle size distribution, pulp density and volume in less than a second. The rate determining step is the time required to obtain the acoustic emission frequency distribution, in this case 10 seconds. Thus the whole analysis process can provide results fast enough to generate a control response.

(d) There is no fundamental difference between the nature of acoustic emission from batch or continuous processes.

TABLE 1

Filter Frequencies and Operation of Third Octave Filter

The third octave filtering system consists of a bank of band-pass filters, the centre frequencies being arranged so that there are 3 filters in each octave.

The filter centre frequencies (KHz) in each (of 8) octaves are tabulated below.

| 1  | 10.0     | 2  | 7.93700 | 3  | 6.29960 |
|----|----------|----|---------|----|---------|
| 4  | 5.0      | 5  | 3.96850 | 6  | 3.14980 |
| 7  | 2.5      | 8  | 1.98425 | 9  | 1.57490 |
| 10 | 1.25     | 11 | 0.99212 | 12 | 0.78745 |
| 13 | 0.625    | 14 | 0.49606 | 15 | 0.39373 |
| 16 | 0.3125   | 17 | 0.24803 | 18 | 0.19786 |
| 19 | 0.15625  | 20 | 0.12402 | 21 | 0.09843 |
| 22 | 0.078125 | 23 | 0.06201 | 24 | 0.04921 |

The output from each of the band-pass filters is squared and passed into an averager. This averager accumulates the data for a specified averaging time and passes this data to the computer.

TABLE 2

| MILLING CONDITIONS FOR BATCH EXPERIMENTS 1 TO 6 | | | | | | | | | |
|---|---|---|---|---|---|---|---|---|---|
| Expt. No. | V1 | D1 | V2 | D2 | V3 | D3 | V4 | D4 | V5 | D5 |
| 1 | 120 | 40 | 90 | 40 | 119 | 25 | 98 | 40 | 92 | 40 |
| 2 | 120 | 40 | 90 | 40 | 115 | 29 | 104 | 40 | 97 | 40 |
| 3 | 120 | 50 | 86 | 50 | 127 | 31 | 96 | 49 | 91 | 49 |
| 4 | 120 | 50 | 96 | 50 | 118 | 36 | 108 | 41 | 103 | 41 |
| 5 | 110 | 50 | 92 | 32 | — | | 96 | 38 | 80 | 37 |
| 6* | 100 | 40 | — | | — | | — | | 100 | 40 |

D1 and D5 are the initial and final % vol Sand in each experiment (D2–D4 are selected intermediate values) V1 and V5 are the initial and final percentage of 'optimal volume' of material in the mill (V2–V4 are selected intermediate values).

We claim:

1. A non-intrusive method for determining a number of inter-related values of physical properties of material within a mill during comminution of the material within the mill wherein the method comprises the steps of:
   (a) detecting an acoustic frequency distribution of milling, in the audio frequency range by utilizing a sound transducer, providing output from said transducer as an analogue electrical signal, the intensity of signal is proportional to the intensity of audio frequency range sound,
   (b) converting the analogue signal to a digital signal,
   (c) passing the digital signal through a digital band-pass filter and selecting at least two frequency bands from the audio frequency range of said digital signal passing through said band-pass filter,
   (d) averaging power in each of the bands for a specified period of time, and
   (e) analysing the averaged power in the bands by utilizing a multivariate statistical technique, thereby obtaining the values of the physical properties.

2. The method according to claim 1 wherein the sound transducer is a microphone.

3. The method according to claim 1 where the properties are selected from the group consisting of particle size distribution of solid particles, pulp density being milled and pulp volume during milling.

4. The method according the claim 1 including amplifying the analogue electrical signal.

5. The method according to claim 1 including passing the analogue electrical signal through a band-pass filter.

6. The method according to claim 5 including removing frequencies above 10 KHz from the audio frequency range of said digital signal passing through said band-pass filter.

7. The method according to claim 5 including removing frequencies below 50 Hz from the audio frequency range of said digital signal passing through said band-pass filter.

8. The method according to claim 5 wherein the band-pass filter is capable of selecting from 2 to 24 desired frequency bands.

9. The method according to claim 1 wherein the multivariate statistical technique is a method of principal components analysis.

10. The method according to claim 1 wherein the multivariate statistical technique is a method of partial least squares.

11. The method according to claim 1 including performing each step on-line.

* * * * *